United States Patent [19]

Bradford

[11] Plant 5,124

[45] Oct. 18, 1983

[54] GENETIC DWARF PEACH TREE - ANDERGEN CULTIVAR

[75] Inventor: Norman Bradford, LeGrand, Calif.

[73] Assignee: Stark Brothers Nurseries and Orchards Company, Louisiana, Mo.

[21] Appl. No.: 348,413

[22] Filed: Feb. 12, 1982

[51] Int. Cl.[3] ..... A01H 5/03

[52] U.S. Cl. ..... Plt./43

[58] Field of Search ..... Plt./43

*Primary Examiner*—Robert E. Bagwill

*Attorney, Agent, or Firm*—Burns, Doane, Swecker & Mathis

[57] ABSTRACT

A new and distinct peach variety which originated by the crossing of an unnamed nectarine seedling No. 16K275 and an unnamed peach seedling No. 54P105 is provided. The new variety is a genetic dwarf which bears early maturing attractive highly blushed medium sized globose fruit which is firm and of mild flavor. When grown at LeGrand, Calif. the fruit commonly ripens at approximately June 15 to 25th.

1 Drawing Figure

SUMMARY OF THE INVENTION

The new and distinct variety of peach tree originated at LeGrand, Calif. through the hand pollination during 1974 of an unnamed nectarine seedling No. 16K275 with pollen from an unnamed peach seedling No. 54P105. The resulting seed from these hand pollinated flowers was germinated in cold frames and was field planted during 1975. Following plant and fruit observations during 1976, trees of the new variety were budded on seedling rootstock for further evaluation. The new variety was initially designated No. 6S225B and was selected by me as being a new and distinct variety because of its distinctive characteristics discussed hereafter.

Trees of the new variety exhibit:

(a) genetic dwarf growth characteristics which form a dense tree growth which is spreading to drooping,
(b) medium vigor,
(c) stocky and shaggy branches and trunk,
(d) large acutely pointed elongated leaves which are of medium thickness and color, and
(e) early ripening firm medium sized highly colored globose fruit of good eating quality.

The fruit of the new variety commonly ripens at approximately June 15 to 25th when grown at LeGrand, Calif. or approximately 48 days earlier than the Elberta peach when grown at the same location.

Asexual propagation of the new variety by budding by me and those acting on my behalf has confirmed that its characteristics come true to form and are established and are transmitted through succeeding generations.

The new variety has been named the ANDERGEN cultivar.

The specimens described herein were grown and observed at LeGrand, Calif.

BRIEF DESCRIPTION OF THE PHOTOGRAPH

The accompanying photograph shows typical specimens of the fruit and foliage of the new variety as depicted in color as nearly true as it it reasonably possible to make the same in a color illustration of this character.

DETAILED DESCRIPTION OF NEW VARIETY

Dates of first and last pickings: June 15 to June 25, 1981 at LeGrand, Calif.

Tree: Small size (6–8′), genetic dwarf; medium vigor; dense; spreading to drooping; productive; regular bearer.

*Trunk.*—Stocky; shaggy.

*Branches.*—Medium stocky; shaggy. Lenticels. — Few; large.

*Leaves.*—Elongated; abruptly pointed; medium thickness; smooth. Length. — Approximately $5\frac{1}{4}$ inches. Width. — Approximately $1\frac{1}{2}$ inches. Color. — Medium green — Ackerman's Green Plate XVIII 35K, Regency Color Standards. Margin. — Glandular; fine. Petiole. — Medium long; medium thick. Glands. — Average number: 4; alternate; large; reniform.

Flowers:

*Date of full bloom.*—Mar. 10, 1981.

*Size.*—Large.

*Color.*—Pink — Rose Pink Plate XI-71V-RR-f, Ridgeway's Color Standards.

Fruit:

*Maturity when described.*—Hard; firm ripe; date — June 17, 1981.

*Size.*—Medium; uniform. Axial diameter. — Approximately $2\frac{1}{4}$ inches. Transverse in suture planes. — Approximately $2\frac{1}{2}$ inches. At right angles to suture planes. — Approximately $2\frac{1}{2}$ inches.

*Form.*—Variable; unsymmetrical; globose; compressed; sides unequal.

*Suture.*—Distinct; extends full length of fruit.

*Ventral surface.*—Rounded; unequal.

*Cavity.*—Abrupt. Depth. — Approximately $\frac{3}{8}$ to $\frac{1}{2}$ inch. Breadth. — Approximately $\frac{1}{2}$ inch.

*Base.*—Oblique to rounded.

*Apex.*—Depressed.

*Stem.*—Approximately $\frac{1}{8}$ inch in length; stout; glabrous.

*Skin.*—Medium thick; tender; some tendency to break at firm ripe. Color. — Highly blushed; approximately 85 to 90 percent Brazil Red — Plate 15-R-i Ridgeway's Color Standards.

*Flesh.*—Color. — Yellow; very slight red near the pit. Texture. — Firm. Fibers. — Fine; tender. Ripens. — Fairly even. Flavor. — Mild; delicate. Aroma. — Wanting. Eating quality. — Very good.

*Stone.*—Semi-free. Size. — Medium. Length. — Approximately 1½ inch. Thickness. — Approximately ⅞ inch. Form. — Oval. Apex. — Acute. Sides. — Equal. Surface. — Furrowed.

Use: Market; dessert.

Keeping quality: Good.

Shipping quality: Good.

I claim:

1. A new and distinct variety of peach tree substantially as illustrated and described, characterized by (a) genetic dwarf growth characteristics which form a dense tree growth which is spreading to drooping, (b) medium vigor, (c) stocky and shaggy branches and trunk, (d) large acutely pointed elongated leaves which are of medium thickness and color, and (e) early ripening firm medium sized highly colored globuse fruit of good eating quality.

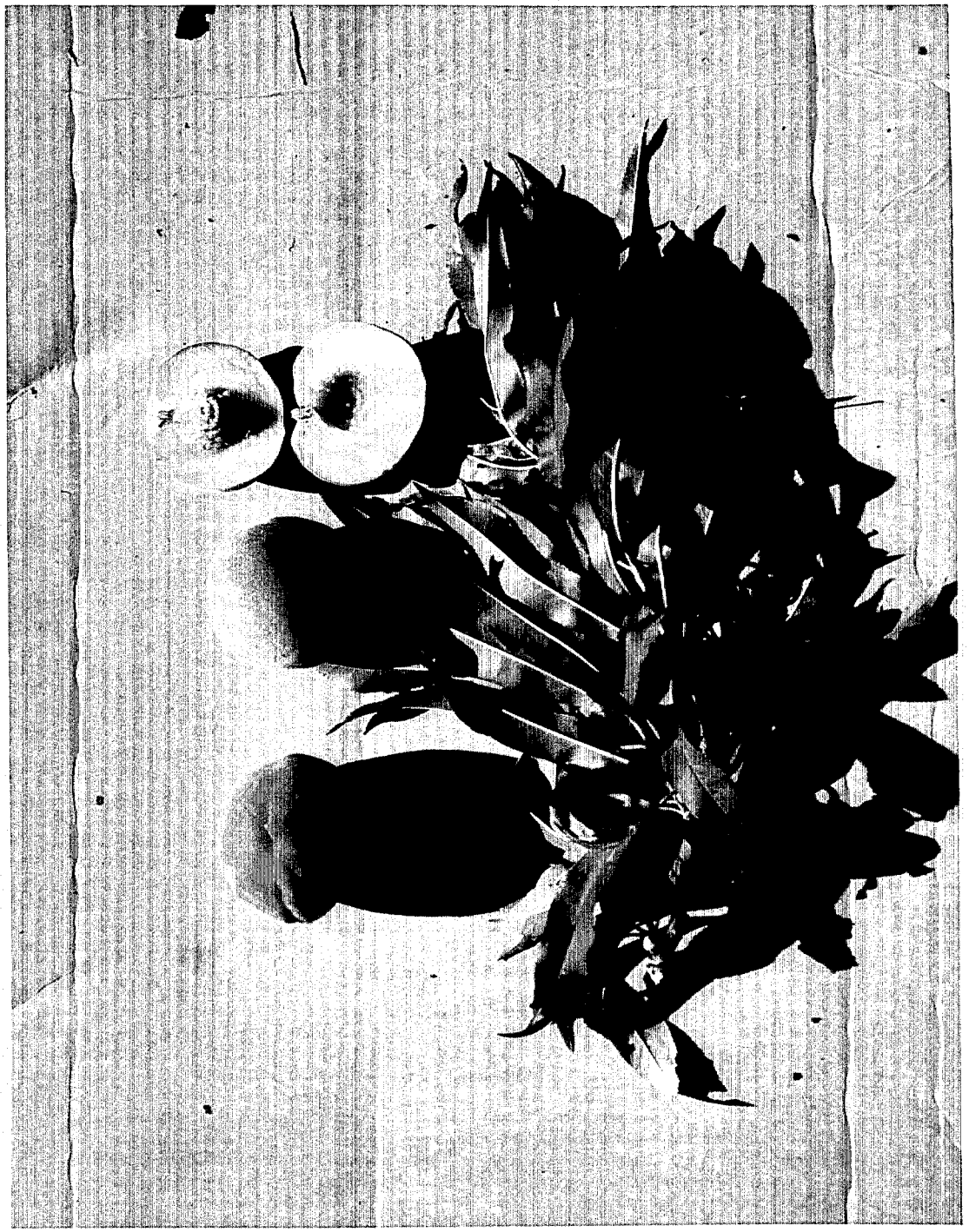

* * * * *